United States Patent
Bonny et al.

(10) Patent No.: US 10,660,721 B2
(45) Date of Patent: May 26, 2020

(54) MODULAR WRIST GUIDE FOR SURGICAL INSTRUMENTS

(71) Applicant: THINK SURGICAL, INC., Fremont, CA (US)

(72) Inventors: Daniel Patrick Bonny, Fremont, CA (US); Saleh Tabandeh, Fremont, CA (US); Michael E. Hoppe, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 268 days.

(21) Appl. No.: 15/555,791

(22) PCT Filed: Mar. 28, 2016

(86) PCT No.: PCT/US2016/024438
§ 371 (c)(1),
(2) Date: Sep. 5, 2017

(87) PCT Pub. No.: WO2016/160660
PCT Pub. Date: Oct. 6, 2016

(65) Prior Publication Data
US 2018/0055591 A1    Mar. 1, 2018

Related U.S. Application Data

(60) Provisional application No. 62/138,981, filed on Mar. 27, 2015.

(51) Int. Cl.
*A61B 34/00* (2016.01)
*A61B 90/53* (2016.01)
(Continued)

(52) U.S. Cl.
CPC ............. *A61B 34/76* (2016.02); *A61B 34/30* (2016.02); *A61B 34/74* (2016.02); *A61B 90/53* (2016.02);
(Continued)

(58) Field of Classification Search
CPC ......... A61B 90/53; A61B 34/30; A61B 90/57; A61B 2034/305; A61B 34/76; A61B 34/20; A61B 34/74
See application file for complete search history.

(56) References Cited

U.S. PATENT DOCUMENTS

| | | | |
|---|---|---|---|
| 4,836,190 A | | 6/1989 | Zwick |
| 5,379,758 A | * | 1/1995 | Snyder ................... A61B 17/02 15/143.1 |

(Continued)

OTHER PUBLICATIONS

Winfree, Kyle N. et al., "A High Fidelity Ungrounded Torque Feedback Device: The iTorqU 2.0", Third Joint EuroHaptics Conference and Symposium on Haptic Interfaces for Virtual Environment and Teleoperator Systems, World Haptics 2009, Mar. 18-20, 2009, pp. 261-266, IEEE (2009).
(Continued)

*Primary Examiner* — Christine H Matthews
*Assistant Examiner* — Joshua Daryl D Lannu
(74) *Attorney, Agent, or Firm* — Blue Filament Law PLLC (57) ABSTRACT

A modular wrist guide is provided that aids a user in operating a hand-held surgical instrument to accurately perform surgical procedures including but not limited to joint arthroplasty. The modular wrist guide acts to constrain the orientation of a hand-held surgical instrument, or a user's wrist relative to the user's forearm to perform a procedure according to a surgical plan. A forearm embracing member is designed to secure the user's forearm to the modular wrist guide.

43 Claims, 5 Drawing Sheets

(51) Int. Cl.
  *A61B 90/57*  (2016.01)
  *A61B 34/30*  (2016.01)
  *A61B 34/20*  (2016.01)

(52) U.S. Cl.
  CPC .............. *A61B 90/57* (2016.02); *A61B 34/20* (2016.02); *A61B 2034/305* (2016.02)

(56) References Cited

U.S. PATENT DOCUMENTS

| | | |
|---|---|---|
| 6,945,252 B2 | 9/2005 | Mengato |
| 8,603,018 B2 * | 12/2013 | Anglada ................. A61F 5/013 |
| | | 473/213 |
| 2005/0121480 A1 | 6/2005 | Cooley |
| 2009/0192511 A1 | 7/2009 | Haffenreffer |
| 2013/0060278 A1 | 3/2013 | Bozung et al. |

OTHER PUBLICATIONS

International Search Report dated Jul. 25, 2016 for International Application No. PCT/US2016/024438 filed Mar. 28, 2016.

\* cited by examiner

MODULAR WRIST GUIDE FOR SURGICAL INSTRUMENTS

CROSS REFERENCE TO RELATED APPLICATIONS

This application claims priority benefit of U.S. Provisional Application Ser. No. 62/138,981 filed 27 Mar. 2015; the contents of which are hereby incorporated by reference.

FIELD OF THE INVENTION

The present invention generally relates to a wearable wrist guide for manipulating a surgical instrument, and more specifically to a guide for constraining the orientation of a surgical instrument relative to a user's forearm to aid in executing a surgical plan.

BACKGROUND OF THE INVENTION

Joint replacement surgery is a medical procedure to replace a patient's degenerated or injured joint with artificial implants. With the advancements in new tools and techniques, the joint replacement procedures have become quite successful in terms of patient satisfaction and implant survival rates. Generally, research has shown that the success of the joint replacement procedure is highly dependent on the final position of the implant. To ensure accurate placement of the implant for an individual patient, robotic and computer-assisted technology have become invaluable tools.

As the mechanical, electrical and computer components of typical robotic systems decrease in size, a new era of robotic hand-held surgical instruments are being developed. With what used to require large robotic systems to create accurate bone cuts can now be accomplished with hand-held systems. For example, the NavioPFS™ Robotic Resurfacing System (Blue Belt Technologies) is a tracked hand-held device that aids a user in performing unicondylar knee replacement. Generally, each system has components programmed to articulate a saw, burr, or cutter to create bone cuts to receive an implant as desired by the user.

Hand-held surgical instruments are normally tracked in space relative to the operative bone to visually show (by way of a monitor) how and where to position or orient the instrument to execute a surgical plan. To create the bone cuts, the user may have to re-orient the instrument such that it is in an operable workspace or along a desired cut plane. For the most part, the user's wrist carries the burden of maintaining and guiding the general position and orientation of the surgical instrument during the procedure. However, the human wrist joint can rotate in three degrees of freedom, which can make it difficult to maintain the device in a specific orientation needed for a given surgical plan.

Additionally, with robotic hand-held surgical instruments, the user must counteract the forces or torques generated by the actuating mechanisms in order for the cutting tool to change position. The user may incorrectly counteract the forces and torques by moving or rotating their wrist rather than holding this instrument grasping hand steady. Therefore, the cutting tool may become misaligned or positioned outside of the operable workspace.

Further, robotic hand-held surgical instruments may be bulky and considerably heavy to handle with one hand thereby leading to fatigue and positional error. The user has to maintain a general position and orientation of the device within an operable workspace or along a desired plane to allow the robotic system to create the cuts accurately. The size and weight of the devices may cause the user to drift outside the operable workspace due to muscle strain and fatigue. Operating times and accuracy may suffer as a result.

Thus, there is a need in the art for a wearable brace that can help guide and maintain a hand-held surgical instrument in a position or orientation to execute a surgical plan. There is a further need for a wearable brace that constrains a user's hand or wrist to provide a stiffer object for the hand-held surgical instrument to actuate against. There is an even further need in the art for a wearable brace to alleviate muscle strain and fatigue created by the weight and size of a hand-held surgical instrument.

SUMMARY OF THE INVENTION

A modular wrist guide system for manipulating a surgical instrument includes a support body with an instrument attachment member at a first end of the support body, and a member that is adapted to embrace a user forearm at a second end of the support body, where at least one orienting mechanism is incorporated with the support body, and at least one orienting mechanism is used to adjust and lock at least one degree of freedom of the surgical instrument relative to the user forearm.

A modular wrist guide system for a surgical instrument includes a support body with a hand embracing member attached to a first end of the support body, and a forearm embracing member attached to a second end of the support body, where there is at least one orienting mechanism incorporated with the support body to adjust and lock at least one degree of freedom of the user's hand relative to the user's forearm.

BRIEF DESCRIPTION OF THE DRAWINGS

The present invention is further detailed with respect to the following drawings that are intended to show certain aspects of the present invention, but should not be construed as a limit on the practice of the present invention.

DETAILED DESCRIPTION OF THE INVENTION

The present invention has utility as a device to aid a user in operating a hand-held surgical instrument to accurately perform surgical procedures including, but not limited to joint arthroplasty. The following description of various embodiments of the invention is not intended to limit the invention to these specific embodiments, but rather to enable any person skilled in the art to make and use this invention through exemplary aspects thereof.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

As used herein, a fiducial marker may either be an active transmitter, such as an LED or electromagnetic emitter, or passive reflector, such as a plastic sphere with a retro-reflective film. A fiducial marker array is an arrangement of two or more fiducial markers in a known geometric relationship in/on a rigid body of any geometric shape; an arrangement of three fiducial markers may be used to resolve all six degrees of freedom (6-DOF) of the rigid body.

The term 'tool' can be any instrument capable of performing work on an external object illustratively including a probe; a drill, a cutter, a bur, a water jet, a laser, or a saw blade for example as well as any assembly used to house and/or operate the instrument.

As used herein, the term 'communication' is to refer to the sending and/or receiving of data and/or energy either through a wireless or electrical connection.

Disclosed herein is the use of a tracking system. The tracking system includes at least one receiver to detect energy either emitted or reflected from a fiducial marker and a processor to calculate one of a position and/or orientation of a fiducial marker. The detectable energy can be for example but not limited to optical, electromagnetic, infrared, ultraviolet, magnetic, fiber optic, ultrasound and targeted visible light. An example of an optical tracking system is the Polaris Spectra® Optical Tracking System (NDI Medical). Also referenced herein are computer-assisted surgical systems, which are to be considered synonymous with computer-aided surgical systems, robotic surgical systems, navigation assisted surgical systems, image-guided surgical systems and the like.

Embodiments disclosed herein make reference to hand-held surgical instruments and systems. Such systems include for example the NavioPFS™ Robotic Resurfacing System (Blue Belt Technologies), the RIO® Robotic System (Mako Surgical Corp.) a navigated freehand saw (TRAK Surgical), the hand held surgical system disclosed in U.S. Pat. Pub. No. 2013/0060278, incorporated by reference herein in its entirety, the articulating hand-held drilling system disclosed in U.S. provisional application 62/054,009 incorporated by reference herein in its entirety, or any other computer-controlled device that requires tracking. It should also be appreciated that other instruments and tools can be utilized by the subject matter disclosed herein including but not limited to power tools, drills, oscillating saws, inline power tools, rotary saws, as well as any other hand-held tools.

Additionally, reference will be made to knee arthroplasty. In total or partial knee arthroplasty, a patient's knee joint is exposed. A surgeon makes multiple planar bone cuts on the distal femur and one planar bone cut on the proximal tibia to receive artificial implants. The surgeon creates the cuts such that when the implants are placed, the desired limb and knee alignments are achieved. Generally, to ensure correct alignment with respect to each individual patient, a surgical plan is created. As used herein, a 'surgical plan' refers to a set of instructions, determined either pre-operatively and/or intra-operatively by a user and/or computer program, which define how and/or where to perform a desired procedure. It should be understood that as knee arthroplasty is used as an exemplary example, other medical and non-medical applications can similarly exploit the subject matter disclosed herein.

With reference to the following figures, embodiments of the present invention provide a modular wrist guide to constrain the orientation of a hand-held surgical instrument or a user's wrist relative to the user's forearm to perform total knee arthroplasty according to a surgical plan. While the following drawings depict a wrist guide as a standalone article, it is appreciated that an inventive wrist guide is readily coupled to a brace (not shown) to support the weight of the present invention; the brace being amenable to securement to a surgical table, an overhead surgical suite fixture, or one worn by the surgeon as for example a belt or a vest. An illustrative example of an embodiment of modular wrist guide 101 is shown generally in FIG. 1. The modular wrist guide 101 has a support body 105 with an instrument attachment member 111 at a first end of the support body 105, a forearm embracing member 107 at the second end of the support body 105, and at least one orienting mechanism 113 incorporated with the support body 105 to adjust and lock at least one degree of freedom of a surgical instrument relative to a user's forearm 103. A coordinate system 115 is also shown, whereby the x-axis represents the longitudinal axis of a user's forearm 103, the y-axis perpendicular to the user's palm, and the z-axis parallel to the axis of an instruments handle. Therefore, roll is referred to as rotation about the x-axis (pronation/supination axis), pitch as rotation about the y-axis (radial/ulnar axis), and yaw as rotation about the z-axis (flexion/extension axis).

Figure 1:
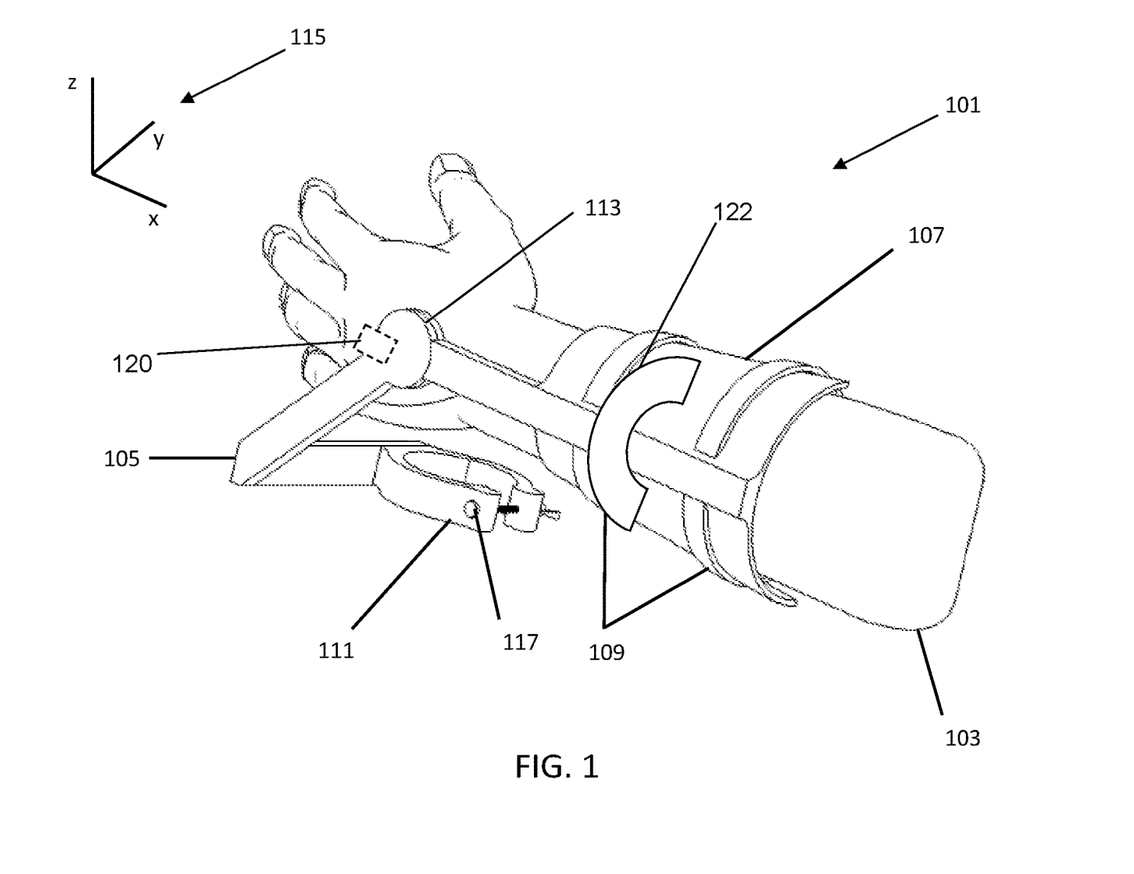
FIG. 1 is a perspective view of a modular wrist guide in accordance with embodiments of the invention.

The forearm embracing member 107 is designed to secure a user's forearm 103 to the modular wrist guide 101. In specific embodiments, the forearm embracing member 107 is semi-circular with straps 109 to fit over a user's forearm 103. The straps 109 are designed to tighten the forearm embracing member 107 to the user's forearm 103 such that the modular wrist guide is securely attached thereto. The straps 109 may secure the user's forearm 103 using a tightening mechanism illustratively including a ratchet strap, hook and loop fastener, a clasp, and combinations thereof. In a specific embodiment, the forearm embracing member 107 fully embraces the user's forearm 103. The user may pull the forearm embracing member 107 over the hand and to the forearm 103 wherein a tightening mechanism secures the modular wrist guide 101 to the user's forearm 103. The forearm embracing member 107 degree of rigidity is a matter of design choice. For example, the forearm embracing member 107 is readily formed from a material illustratively including neoprene, rubber, spandex, ABS plastic, polyurethane, aluminum, titanium, stainless steel, and combinations thereof. It should be appreciated that as only one configuration of the forearm embracing member 107 is shown in FIG. 1, other designs and/or configurations can similarly attach the modular wrist guide 101 to a user's forearm 103 without deviating from the scope of the invention.

The forearm embracing member 107 is attached and/or incorporated with the second end of a support body 105. The forearm embracing member 107 may be attached and/or incorporated to the second end of the support body 105 by way of a fastener illustratively including screws, rivets, clamps, staples, and combinations thereof. For example, the forearm embracing member 107 may be made of a rigid plastic or metal, where the second end of the support body screws directly into the forearm embracing member 107. The forearm embracing member 107 may contain a sleeve that the second end of the support body 105 may slip into and be secured in a similar manner. In an alternative embodiment, the forearm embracing member 107 and the second end of the support body 105 are a unitary structure.

An instrument attachment member 111 is incorporated with and/or attached to the first end of the support body 105.

The instrument attachment member 111 may be fastened to the support body 105 by fasteners illustratively including screws, rivets, clamps, and combinations thereof. In an alternative embodiment, the instrument attachment member 111 and support body 105 are a unitary structure. The instrument attachment member 111 is designed to removably attach a surgical instrument to the modular wrist guide 101. The instrument attachment member 111 includes a fastening element 117 illustratively having a clamp, clasp, tether, quick connect mechanisms, and combinations thereof. The fastening element 117 may include a tightening mechanism for example a screw and wing-nut, ratchet mechanism, and combinations thereof to rigidly secure an instrument to the modular wrist guide 101. The instrument attachment member 111 is configured to allow the user to comfortably hold the handle of the instrument while the instrument is secured to the modular wrist guide 101. For example, as shown in FIG. 1, the instrument attachment member 111 is located just below the user's hand. Alternatively, the instrument attachment member 111 may be located to the side or above the user's hand. Furthermore, multiple instrument attachment members may be attached and/or incorporated with the support body, such as one below and one above the user's hand. In a particular embodiment, the instrument attachment member 111 may be shaped or configured in a manner that easily receives a surgical instrument illustratively including a snap fastener, and combinations thereof. For example, the surgical instrument may include a small receiving element on the bottom or side of the handle. In a specific embodiment the instrument attachment member 111 may have a complementary mate that inserts or attaches and locks in the receiving element. In specific embodiments, the instrument attachment member 111 is configured to attach to a plurality of instruments such that the user does not have to remove or adjust the modular wrist guide 101 when a new instrument is needed by the user.

Incorporated with the support body 105, is at least one orienting mechanism 113 to adjust and lock at least one degree of freedom of the surgical instrument relative to the user's forearm 103. As shown in FIG. 1, the orienting mechanism 113 may change the pitch of the surgical instrument when the surgical instrument is securely attached to the instrument attachment member 111. The orienting mechanism 113 including components that allow the surgical instrument to rotate and lock in a specified or desired orientation relative the user's forearm 103. For example, the orienting mechanism 113 may be a ratchet with gears and pawls, where the user may manually or passively adjust and lock the position of the surgical instrument at a desired or specified orientation. In a specific embodiment the orienting mechanism 113 may be one of a ratchet, rotary joint, motor, step motor, revolute joint, prismatic joint, or spherical joint. The user may then re-adjust the orientation by disengaging the pawl by, for example, by pressing a button or pulling a lever. The orienting mechanism 113 may by a set of pulleys and cables that may adjust the orientation of a surgical instrument.

In specific embodiments, the orienting mechanism 113 may be controlled by electrical mechanisms formed with components illustratively including actuators, gear motors, gears, worm gears, step motors, servo motors, and combinations thereof. Buttons in communication with a controller 120 may be used to control the rotation of the orienting mechanism 113, and the buttons may be located on the orienting mechanism 113, on the support body 105, or on the forearm embracing member 107. Therefore, the user may easily and very precisely adjust and lock the surgical instrument in a desired or specified orientation relative to the user's forearm 103. In specific embodiments, the orienting mechanism 113 is coaxial with the radial/ulnar rotation axis of a user's wrist joint. In particular embodiments, the orienting mechanism 113 may be controlled by a combination of manual and electrical mechanisms.

The desired or specified orientation of an attached surgical instrument relative to the user's forearm is generally based on the execution of a surgical plan. For example, in total knee arthroplasty, five planar cuts are created on the distal femur, the cuts including the distal femur, anterior femur, posterior femur, anterior chamfer, and posterior chamfer cuts. A pre-operative or intra-operative plan is created for each patient such that the planes, as a whole, are precisely cut to receive the implant in a position and orientation that achieves the desired limb and knee alignments. For this application, the desired or specified orientation of the surgical instrument relative to the user's forearm 103 may be based on the particular planar cuts. For example, to create the anterior femoral cut, the desired or specified orientation may be in a neutral position as depicted in FIG. 1, and then in order to create the anterior chamfer cut, a surgical instrument may be rotated, by way of orienting mechanism 113, about the radial/ulnar axis and locked in place such that the working portion of the tool (i.e., burr, cutter, saw blade) is aligned with the anterior chamfer cut plane. Each cut plane having a desired or specified surgical instrument orientation where the modular wrist guide 101 constrains the user such that the working end of the surgical instrument is aligned with the particular cut plane. Thus, the user is guided and may maintain the surgical instrument in a desired or specified position and/or orientation to accurately create each bone cut according to the surgical plan.

Additionally, since the user's hand is grasping the surgical instrument, the wrist of the user is constrained to the desired or specified orientation relative to the user's forearm 103. By constraining the user's wrist in a desired or specified orientation, a robotic hand-held surgical instrument has a stiffer platform to actuate against to precisely execute the bone cuts according to the surgical plan. For example, the robotic hand-held surgical instrument may need to actuate a tool in a certain direction with respect to the surgical plan. Without the modular wrist guide 101, the user may incorrectly counteract the forces and torques generated by the actuating mechanisms by moving or rotating their wrist rather than holding their hand steady. With the modular wrist guide 101 constraining the user's wrist, the user's hand remains steady in the desired or specified orientation and the robotic hand held surgical instrument can more effectively actuate the tool. Additionally, the weight of the surgical instrument is now distributed along the modular wrist guide 101 and to the forearm as opposed to only the user's wrist alleviating any muscle strain and fatigue that could otherwise affect the procedure.

Figure 2A:
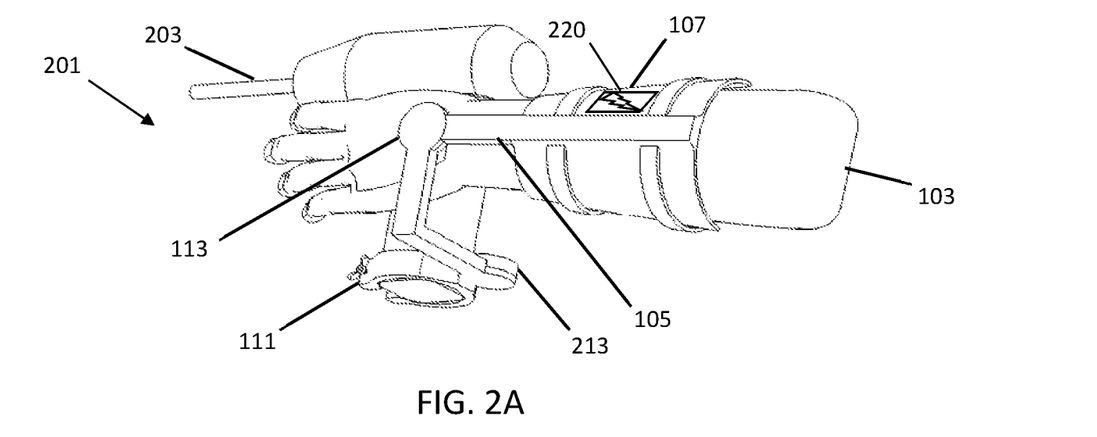
FIGS. 2A and 2B are perspective views of an embodiment of a modular wrist guide with two orientation mechanisms in accordance with an embodiment of the invention.
Figure 2B:
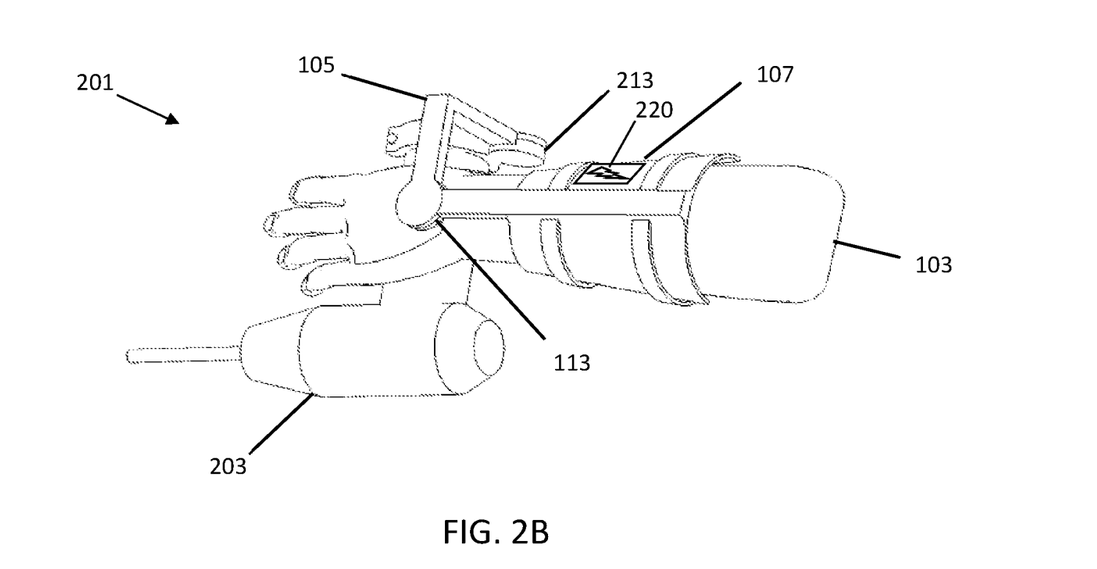

Referring to FIGS. 2A and 2B, an embodiment of a modular wrist guide 201 with an additional orienting mechanism 213 is incorporated with the support body 105. The additional orienting mechanism 213 may likewise include components of orienting mechanism 113. However, as shown in FIG. 2A, the user may adjust and lock the yaw of a surgical instrument relative to a user's forearm 103. Therefore, the yaw of a surgical instrument and the user's wrist, when grasping the surgical instrument, are constrained. When adding orienting mechanism 213 with orienting mechanism 113, the user's wrist may be constrained in two degrees of freedom. Depending upon the complexity of the surgical plan as well as the desired cuts that need to be performed, the robotic hand-held surgical instrument may need to actuate the tool in multiple degrees of freedom. In a particular embodiment, the orienting mechanism 213 is coaxial with the flexion/extension rotation axis of a user's wrist joint as depicted in FIG. 2A. It is appreciated that a computer interfaced controller operating an actuator (not shown) is provided in some inventive embodiments that selectively opens, locks, or moves the orienting mechanism 113 for a specific phase of a given surgical plan. The forearm embracing member may be configured to removably attach a power supply 220 for the surgical instrument.

With respect to FIGS. 2A and 2B, a surgical instrument 203 is rigidly attached to the instrument attachment member 111 of the modular wrist guide 201. As shown, with two orienting mechanisms 113 and 213, the surgical instrument 203 may be fully inverted and remain in an operable orientation without removing or adjusting the forearm embracing member 107 from the user. In FIG. 2A the working portion of the surgical instrument 203 is above the user's wrist, while in FIG. 2B the working portion of the surgical instrument 203 is below the user's wrist. In total knee arthroplasty, it is common for a user to maneuver a surgical saw in these two configurations to create different planar cuts. Therefore, the ability to invert the surgical instrument without removing or adjusting the forearm embracing member 107 is a highly desirable feature provided by embodiments of the inventive modular wrist guide 201. In the inverted position, the orienting mechanisms 113 and 213 may still be adjusted and locked in a desired or specified orientation to constrain the user's wrist in at least one degree of freedom. It is appreciated that a computer interfaced controller operating an actuator (not shown) is provided in some inventive embodiments that selectively opens, locks, or moves an orienting mechanism 113 or 213 for a specific phase of a given surgical plan.

It should be appreciated that additional orienting mechanisms may be incorporated with the support body 105 to constrain additional degrees of freedom. Likewise, additional orienting mechanisms on the support body 105 may allow for redundant degrees of freedom to enhance the comfort or ease of use in positioning and/or orienting a surgical instrument relative to a user's forearm 103 to perform a surgical procedure. Additionally, linear or prismatic mechanisms may also be incorporated with the support body 105 to extend/retract the support body 105, forearm attachment member 107, and/or instrument attachment member 111. The linear mechanisms may allow the user to adjust the distance between forearm embracing member 107 and the surgical instrument for comfort or to perform a portion of a surgical procedure.

Figure 3A:
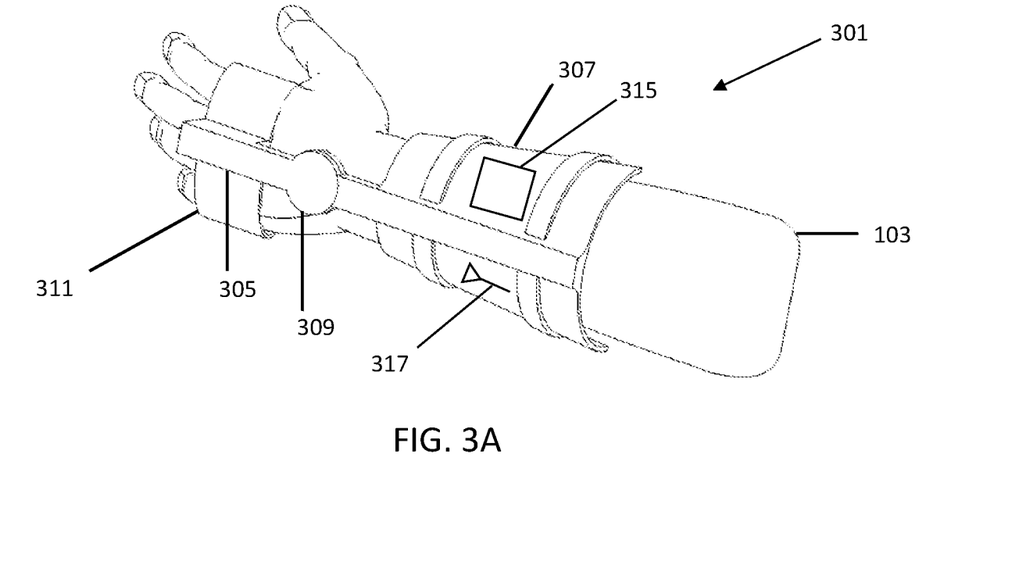
FIGS. 3A and 3B are perspective views of another embodiment of a modular wrist guide in accordance with embodiments of the invention.
Figure 3B:
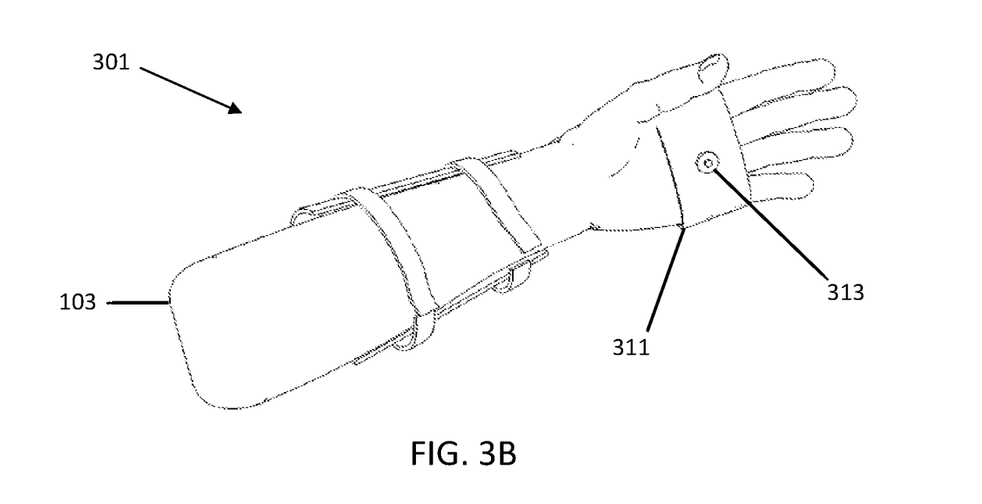

An embodiment of a modular wrist guide 301 is shown in FIGS. 3A and 3B. The modular wrist guide 301 includes a support body 305, a forearm embracing member 307 on a second end of the support body 305, a hand embracing member 311 at a first end of the support body 305, an instrument attachment member 313 incorporated with the hand embracing member 311 and at least one orienting mechanism 309 incorporated with the support body 305 to adjust and lock at least one degree of freedom of a user's wrist relative to the user's forearm 103. The forearm embracing member 307, support body 305, and the at least one orienting mechanism 309 may be constructed similar to that of modular wrist guide 101. The hand embracing member 311 is configured to rigidly embrace and/or attach about a user's hand such that the user's wrist may be constrained in a desired or specified orientation by the orienting mechanism 309. On the palm of the hand embracing member 311 is an instrument attachment member 313 to receive a surgical instrument. The instrument attachment member 313 may be similar to that of the modular wrist guide 101. In a specific inventive embodiment, the instrument attachment member 313 interacts with a receiving portion on the handle of a surgical instrument. For example, the handle of the surgical instrument may include one part of a snap fastener, while the hand embracing member 311 includes the complementary part of the snap fastener. Therefore, the surgical instrument may easily snap and attach to the hand embracing member 311 and be firmly gripped by the user. Multiple snap fasteners may be used to ensure the surgical instrument is secured to the hand embracing member 311. Additionally, a rigid strap (not shown) including complementary fasteners may be strapped to a variety of surgical instruments in the operating room. Therefore, each surgical instrument would be compatible with the modular wrist guide 301. It is appreciated that a computer interfaced controller operating an actuator (not shown) is provided in some inventive embodiments that selectively opens, locks, or moves the orienting mechanism 309 for a specific phase of a given surgical plan.

Continuing with FIG. 3A, the orienting mechanism 309 adjusts and locks a degree of freedom of the user's hand relative to the user's forearm 103. In both the modular wrist guide configurations 101 and 301, the user's wrist is constrained in a desired or specified orientation to allow the hand-held surgical instrument to execute a surgical plan. Therefore, the user is guided and may maintain a position and orientation of the surgical instrument while providing additional support for the actuation of the tool (i.e., cutter, burr, saw blade) of the hand-held surgical instrument against the user's wrist and/or hand.

Adjustment and Locking Methods

In specific inventive embodiments, the user may manually adjust and lock the orientation of the surgical instrument or the user's hand relative to the user's forearm that feels most comfortable for a particular cut. For example, a monitor may display a particular planar cut on the knee. The user then places the working end of the surgical instrument in the orientation of the planar cut. Subsequently and prior to cutting, the user manually adjusts and locks the orienting mechanism(s) (113, 213, 309) such that the user's forearm, wrist, hand, shoulder and/or body are positioned as the user desires while still constraining the surgical instrument or user's wrist in the particular planar orientation. In a specific embodiment, the monitor may display an operable workspace that the surgical instrument must occupy. The user may position the surgical instrument in the operable workspace and prior to cutting, adjust and lock the orienting mechanism(s) in a comfortable position as determined by the user.

The orienting mechanisms, for example, 113, 213, 309 and any additional orienting or linear mechanisms may be adjusted and locked into place passively based on the movements of the user's hand, wrist and/or forearm. For example, once the modular wrist guide is attached to the user's forearm 103, the user may rotate their wrist in a desired or specified position wherein the orienting mechanisms freely rotate, translate and/or ratchet and lock in the position. The position may then be constrained passively from, for example, a ratchet mechanism or may be further constrained by, for example, pressing a button or pushing/pulling a lever that further engages the locking mechanism. The locking mechanism may then be disengaged and set to a passive orientating state to adjust the surgical instrument to a new position and/or orientation.

In specific inventive embodiments, the orienting mechanisms 113, 213, 309 may include active mechanical and electrical components illustratively including actuation motors, gear motors, step motors, servo motors, gears, worm gears, power supplies, screws, micro-motors, and combinations thereof. The user may control the electrical components, and therefore a desired or specified orientation, using input parameters located on the modular wrist guide. For example, the input parameters may be buttons which are designated by their respective direction of rotation. In specific embodiments, the input parameters are located on an external device. The external device, for example may be a display, a monitor, remote control, joystick, a computer interface, or a combinations thereof. In one embodiment, the external device may be a user interface 315 located on the forearm embracing member 307. The user interface on the forearm embracing member may additionally be in wireless or electrical communication with the surgical instrument, the modular wrist guide, or other external devices, such as a computer operating software associated with specific phases of the surgical plan. The user interface may provide the user with a multitude of data or input/output parameters, for example but not limited to the surgical instrument control parameters, battery life, rotational velocity of the tool, patient information, input parameters to control the orienting mechanisms 113, 213, 309, the status of the surgical instrument, the progress of a procedure, the alignment of the tool relative to the surgical plan, operating instructions, and any combinations thereof. In a particular inventive embodiment, the modular wrist guide may include wireless receivers and transmitters 317 to receive and send data through for example, Bluetooth, WLAN, radiofrequency, and visible light communication.

Figure 4:
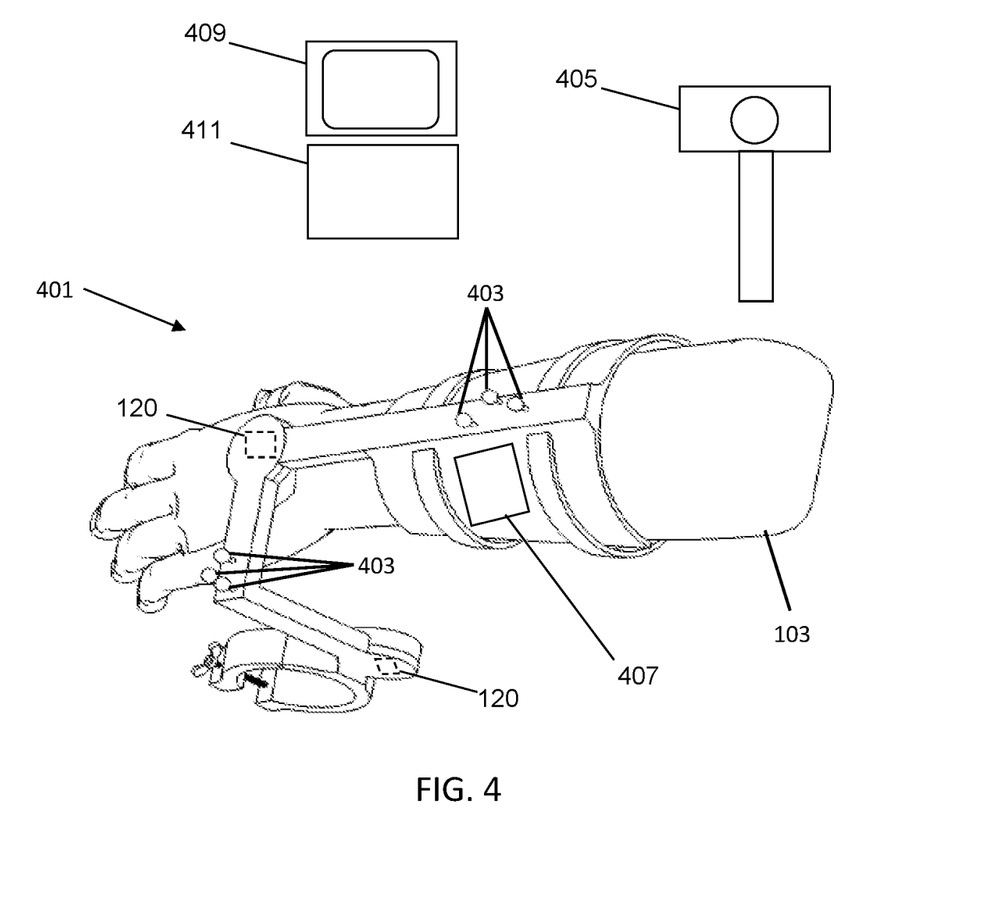
FIG. 4 illustratively depicts fiducial markers attached to the modular wrist guide of FIGS. 2A and 2B for tracking in accordance with embodiments of the invention.

With respect to FIG. 4, the inventive embodiment modular wrist guide 401 includes active or passive fiducial markers 403. The fiducial markers 403 may be placed on various parts of the modular wrist guide 401 to be tracked in space with one or more tracking systems 405. The fiducial markers 403 may be attached to a separate rigid body, known as a marker array, which may be fixed to one or more locations on the modular wrist guide 401. The tracking system 405 may then track the position and orientation of the modular wrist guide, and therefore a user's forearm 103, wrist, and/or hand in space during the procedure. A user interface 407 incorporated with said forearm embracing member and in communication with at least one of a surgical instrument or a tracking system.

A monitor 409 may then display the modular wrist guide 401 on the screen to aid the user in adjusting and locking the orientation of the surgical instrument or user's wrist relative to a user's forearm 103. The display may show the modular wrist guide 401 in multiple configurations that places the working end of the surgical instrument along a planar cut or in an operable workspace.

In specific inventive embodiments, a computing controller 411 is wirelessly or electrically connected to the surgical instrument and the modular wrist guide 401. A tracking system, such as the Polaris® Spectra® (NDI Medical), is in communication with the controller and tracks the position and orientation of the surgical instrument, modular wrist guide and patient's anatomy. From the data collected from the tracking system, the controller ensures the surgical instrument executes the surgical plan relative to the patient's anatomy precisely. Similarly, the controller may control the orienting mechanisms 113, 213, and 309 such that the user is actively guided and/or constrained to a specified position and/or orientation to perform at least a portion of a surgical procedure. A processor in communication with the controller continually updates the transformation matrix between the patient's anatomy, the surgical instrument, and the modular wrist guide such that their positions and orientations are known relative to each other throughout the procedure. The controller 120 may then update the position and orientation of the surgical instrument and/or the modular wrist guide 401 such that the surgical plan is executed as designed by the user.

Figure 5:
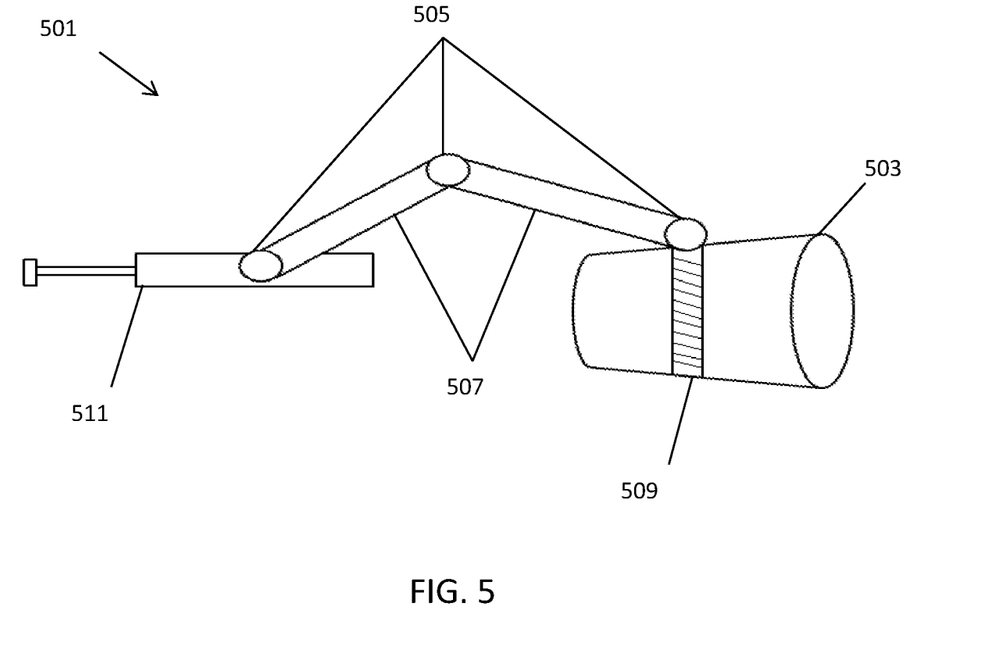
FIG. 5 depicts an embodiment of a hand-held robotic system in accordance with embodiments of the invention.

In specific embodiments, the modular wrist guide may be the robotic system 501 as shown in FIG. 5. The robotic system 501 may include a brace 503 to interact with the user's forearm, at least one orienting mechanism or joint 505, at least one link 507, and an end effector 511. The robotic system 501 may further include a revolute joint 509 coincident about the user's forearm to rotate the end-effector about the user's forearm. The robotic system 501 has at least one degree of freedom and is worn with a brace 503 on the forearm. The end effector 511 is held by the surgeon wherein the robotic system may compensate for the vibration and errors of the hand of the surgeon through the articulation of the various joints 505, 509 and links 507. The actuation of the orienting mechanisms or joints may be controlled at the base of the robotic system 501, on the braces, and transferred to the joints through mechanisms illustratively including belts, chains, or cables. It should be appreciated that the use of belts, chains, and/or cables reduces the overall weight of the robotic system. A motor may be located at the base which may transmit the actuation to each joint. The orienting mechanism or joint 505 may be located near the braces and may be active or passive but should allow adjustment of the device for a comfortable posture for the surgeon. The base of the robot may rotate around the braces so the arm can bring the tool to the surgeon's hold from under the wrist. In specific embodiments, the robot arm may be compliant on demand to be used as a coordinate measuring machine, a registration device, and/or a digitization device. In specific embodiments, the robot arm may be used as a slave manipulator of a haptic device. For example, the user may hold a joystick or controller which actuates the arm. The arm in this case may be longer to accommodate enough space for the user to hold the joystick or controller. The robotic system 501 may be operated manually, electrically, pneumatically or a combination thereof. The orienting mechanism or joints 501 may be actuated by a controller electrically or wirelessly connected to the robotic system 501. In specific embodiments, the robotic system may have markers attached such that the robotic system is tracked in space. A controller may further actuate the joints 505 such that a desired cut plane and/or cut geometry is maintained while a user manipulates the end effector 511.

In specific embodiments, a haptic device 122 (see FIG. 1) may also be attached to the modular wrist guide (101, 201, 301, 401) such as on the forearm embracing member (107, 307). A haptic device generates forces and torques that may passively guide the user in positioning and orienting the surgical instrument in a specified location. Haptic devices generally have one or more gyroscopes similar to the gyroscope described in Winfree, K. et al.: "A high fidelity ungrounded torque feedback device: The iTorqU 2.0," Third Joint Eurohaptics Conference and Symposium on Haptic Interfaces for Virtual Environment and Teleoperator Systems Salt Lake City, Utah, USA, pp. 261-266, 18-20 Mar. 2009. The haptic device is in communication with one or more controllers and/or computers such that forces and/or torques are generated to passively guide the user's wrist and/or forearm based on the surgical plan.

Feedback Mechanisms

The modular wrist guide or robotic system provides a guide to aid the user in accurately performing a medical procedure. In specific embodiments, the desired or specified position and/or orientation may be relayed to the user using a feedback mechanism. The feedback mechanism may be linked to a surgical plan. Examples of feedback mechanisms illustratively include a visual display such as a monitor, heads up display (HUD) unit, Google glasses and/or a virtual reality environment. The visual display may relay to the user how the joints or orienting mechanisms need to be positioned and/or oriented such that the surgical instrument can perform at least a phase of a surgical plan. Another feedback mechanism illustratively includes an audible signal directing the user how and where to orient the orienting mechanisms and/or joints. The feedback mechanism may further be a controller 120 as shown in FIG. 1 embedded in the orienting mechanism and/or joints that automatically or semi-automatically positions or orients the orienting mechanism and/or joints of the modular wrist guide 101, 201, 301, 401 or robotic system 501 according to a phase of a surgical plan. In specific embodiments, a visual, audio, semi-automatic, or automatic control and any combination thereof is used to provide feedback to the user as to the desired or specified position and/or orientation of the modular wrist guide 101, 201, 301, 401 or robotic system 501. The feedback mechanism may also be generated by teaching a hand-held robotic system or the robotic system 501 a desired cut plane, cut geometry, or any other desired movements. For example, the user may touch two points on a work piece with the end effector to define a planar cut. The system records the two points whereby the feedback mechanism provides a visual display, audible signals, or automatically or semi-automatically controls the joints or orienting mechanisms such that the planar cut can be created accurately.

Other Embodiments

Embodiments of the modular wrist guide may further include an upper arm and/or shoulder attachment for increased stability and control of the surgical instrument. In a particular embodiment the modular wrist guide is an exoskeleton about a user's arm with the surgical instrument attached at a working end. The exoskeleton may be haptically or actively controlled for vibration damping and/or guidance. Additionally, the modular wrist guide may include a power supply attachment member. For example, on the forearm embracing member, straps, clips, clamps, VELCRO® and combinations thereof are designed to receive a power supply that may provide power to the surgical instrument and/or to the orienting mechanisms of the modular wrist guide.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A modular wrist guide system for manipulating a surgical instrument comprising:
a support body;
an instrument attachment member at a first end of said support body;
a member adapted to embrace a user forearm at a second end of said support body; and
at least one orienting mechanism incorporated with said support body, where said at least one orienting mechanism is used to adjust and lock at least one degree of freedom of the surgical instrument relative to the user forearm; and
a feedback mechanism configured to determine the at least one degree of freedom using at least one of a visual signal, an audible signal, semi-automatic control, or automatic control.

2. The modular wrist guide system of claim 1 wherein said at least one orienting mechanism rotates in at least one of pitch, roll, yaw, or a combination thereof.

3. The modular wrist guide system of claim 1 wherein said instrument attachment member further comprises a fastening element configured to receive a variety of surgical instrument types.

4. The modular wrist guide system of claim 1 further comprising a power supply; and
wherein said forearm embracing member is configured to removably attach the power supply to provide power for the surgical instrument.

5. The modular wrist guide system of claim 1 wherein said at least one orienting mechanism is one of a ratchet, rotary joint, motor, step motor, revolute joint, prismatic joint, or spherical joint.

6. The modular wrist guide system of claim 1 further comprising a haptic device, where said haptic device is attached to the second end of said support body and provides haptic feedback to the user in positioning and orienting the surgical instrument.

7. The modular wrist guide system of claim 1 wherein said at least one orienting mechanism is electrically controlled.

8. The modular wrist guide system of claim 1 further comprising at least one fiducial marker that is attached to said modular wrist guide system, said at least one fiducial marker in communication with a tracking system.

9. The modular wrist guide system of claim 1 further comprising a user interface incorporated with said forearm embracing member and in communication with at least one of the surgical instrument or a tracking system.

10. A modular wrist guide system for manipulating a surgical instrument comprising:
a support body;
an instrument attachment member at a first end of said support body;
a member adapted to embrace a user forearm at a second end of said support body;
at least one orienting mechanism incorporated with said support body, where said at least one orienting mechanism is used to adjust and lock at least one degree of freedom of the surgical instrument relative to the user forearm; and
a haptic device, where said haptic device is attached to the second end of said support body and provides haptic feedback to the user in positioning and orienting the surgical instrument.

11. The modular wrist guide system of claim 10 wherein said instrument attachment member further comprises a fastening element configured to receive a variety of surgical instrument types.

12. The modular wrist guide system of claim 10 wherein said forearm embracing member is configured to removably attach a power supply for the surgical instrument.

13. The modular wrist guide system of claim 10 wherein said at least one orienting mechanism is electrically controlled.

14. The modular wrist guide system of claim 10 further comprising at least one fiducial marker that is attached to said modular wrist guide system, said at least one fiducial marker in communication with a tracking system.

15. The modular wrist guide system of claim 10 further comprising a user interface incorporated with said forearm embracing member and in communication with at least one of the surgical instrument or a tracking system.

16. A modular wrist guide system for manipulating a surgical instrument comprising:
   a support body;
   an instrument attachment member at a first end of said support body;
   a member adapted to embrace a user forearm at a second end of said support body;
   at least one orienting mechanism incorporated with said support body, where said at least one orienting mechanism is used to adjust and lock at least one degree of freedom of the surgical instrument relative to the user forearm; and
   wherein said at least one orienting mechanism is electrically controlled.

17. The modular wrist guide system of claim 16 wherein the at least one degree of freedom is determined by a feedback mechanism.

18. The modular wrist guide system of claim 16 wherein said instrument attachment member further comprises a fastening element configured to receive a variety of surgical instrument types.

19. The modular wrist guide system of claim 16 wherein said forearm embracing member is configured to removably attach a power supply for the surgical instrument.

20. The modular wrist guide system of claim 16 further comprising at least one fiducial marker that is attached to said modular wrist guide system, said at least one fiducial marker in communication with a tracking system.

21. The modular wrist guide system of claim 16 further comprising a user interface incorporated with said forearm embracing member and in communication with at least one of the surgical instrument or a tracking system.

22. A modular wrist guide system for manipulating a surgical instrument comprising:
   a support body;
   an instrument attachment member at a first end of said support body;
   a member adapted to embrace a user forearm at a second end of said support body;
   at least one orienting mechanism incorporated with said support body, where said at least one orienting mechanism is used to adjust and lock at least one degree of freedom of the surgical instrument relative to the user forearm; and
   at least one fiducial marker that is attached to said modular wrist guide system, said at least one fiducial marker in communication with a tracking system.

23. The modular wrist guide system of claim 22 wherein at least one of a position or orientation of a modular wrist guide is displayed on a monitor in relation to a working end of said surgical instrument along a planar cut or in an operable workspace as determined by the tracking system.

24. The modular wrist guide system of claim 22 wherein the at least one orienting mechanism is actively controlled by a controller and the at least one degree of freedom is adjusted and locked in an orientation based on at least one of 1) the execution of at least a portion of a surgical plan or 2) the position and orientation of a modular wrist guide as determined by the tracking system.

25. The modular wrist guide system of claim 22 wherein the at least one degree of freedom is determined by a feedback mechanism.

26. The modular wrist guide system of claim 22 wherein said instrument attachment member further comprises a fastening element configured to receive a variety of surgical instrument types.

27. The modular wrist guide system of claim 22 wherein said forearm embracing member is configured to removably attach a power supply for the surgical instrument.

28. The modular wrist guide system of claim 22 wherein said at least one orienting mechanism is electrically controlled.

29. The modular wrist guide system of claim 22 further comprising a user interface incorporated with said forearm embracing member and in communication with at least one of the surgical instrument or the tracking system.

30. A modular wrist guide system for manipulating a surgical instrument comprising:
   a support body;
   an instrument attachment member at a first end of said support body;
   a member adapted to embrace a user forearm at a second end of said support body;
   at least one orienting mechanism incorporated with said support body, where said at least one orienting mechanism is used to adjust and lock at least one degree of freedom of the surgical instrument relative to the user forearm; and
   a user interface incorporated with said forearm embracing member and in communication with at least one of the surgical instrument or a tracking system.

31. The modular wrist guide system of claim 30 wherein said user interface has an input parameter to adjust the at least one degree of freedom of the surgical instrument.

32. The modular wrist guide system of claim 30 wherein the at least one degree of freedom is determined by a feedback mechanism.

33. The modular wrist guide system of claim 30 wherein said instrument attachment member further comprises a fastening element configured to receive a variety of surgical instrument types.

34. The modular wrist guide system of claim 30 wherein said forearm embracing member is configured to removably attach a power supply for the surgical instrument.

35. The modular wrist guide system of claim 30 wherein said at least one orienting mechanism is electrically controlled.

36. The modular wrist guide system of claim 30 further comprising at least one fiducial marker that is attached to said modular wrist guide system, said at least one fiducial marker in communication with the tracking system.

37. A modular wrist guide system for a surgical instrument comprising:
   a support body;
   a hand embracing member attached to a first end of said support body;
   a forearm embracing member attached to a second end of said support body; and at least one orienting mechanism incorporated with said support body to adjust and lock at least one degree of freedom of a user's hand relative to the user's forearm; and a feedback mechanism configured to determine the at least one degree of freedom using at least one of a visual signal, an audible signal, semi-automatic control, or automatic control.

38. The modular wrist guide system of claim 37 further comprising an instrument attachment member incorporated with said hand embracing member.

39. The modular wrist guide system of claim 38 wherein said instrument attachment member is configured to receive a plurality of surgical instruments.

40. The modular wrist guide system of claim 37 further comprising a power supply; and wherein said forearm embracing member is configured to removably attach the power supply to provide power for the surgical instrument.

41. The modular wrist guide system of claim 37 wherein said at least one orienting mechanism is electrically controlled.

42. The modular wrist guide system of claim 37 further comprising at least one fiducial marker that is attached to said modular wrist guide system, said at least one fiducial marker in communication with a tracking system.

43. The modular wrist guide system of claim 37 further comprising a user interface incorporated with said forearm embracing member and in communication with at least one of the surgical instrument or a tracking system.

* * * * *